(12) United States Patent
Steiner et al.

(10) Patent No.: US 6,222,034 B1
(45) Date of Patent: Apr. 24, 2001

(54) 3-SUBSTITUTED PYRIDO[4',3':4,5]THIENO[2, 3-D]PYRIMIDINE DERIVATIVES, THEIR PREPARATION AND THEIR USE

(75) Inventors: Gerd Steiner, Kirchheim; Wilfried Lubisch, Mannheim; Alfred Bach, Heidelberg; Franz Emling, Ludwigshafen; Karsten Wicke, Altrip; Hans-Jürgen Teschendorf, Dudenhofen; Berthold Behl, Limburgerhof, all of (DE); Sharon Cheetham; Frank Kerrrigan, both of Nottingham (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,449

(22) PCT Filed: Aug. 22, 1997

(86) PCT No.: PCT/EP97/04593

§ 371 Date: Mar. 10, 1999

§ 102(e) Date: Mar. 10, 1999

(87) PCT Pub. No.: WO98/11110

PCT Pub. Date: Mar. 19, 1998

(30) Foreign Application Priority Data

Sep. 10, 1996 (DE) .............................. 196 36 769

(51) Int. Cl.$^7$ ...................... C07D 495/14; A61K 31/519; A61K 31/435
(52) U.S. Cl. ............................ 544/250; 514/267
(58) Field of Search ............................ 544/250; 514/267

(56) References Cited

U.S. PATENT DOCUMENTS

| | | | |
|---|---|---|---|
| 3,627,766 | * 12/1971 | Eichenberger et al. | ............. 544/250 |
| 3,823,151 | * 7/1974 | Eichenberger et al. | ......... 544/250 X |
| 4,695,568 | * 9/1987 | Ninomiya et al. | ..................... 514/258 |
| 4,835,157 | 5/1989 | Press et al. | ........................ 514/258 |
| 4,959,368 | * 9/1990 | Awaya et al. | ....................... 514/252 |

FOREIGN PATENT DOCUMENTS

| | | |
|---|---|---|
| 0272079 | * 9/1984 | (DE) . |
| 0272086 | * 9/1989 | (DE) . |
| 0272088 | * 9/1989 | (DE) . |
| 329 168 | 8/1989 | (EP) . |

OTHER PUBLICATIONS

Arch Pharm. (1995) 352:451–454, Fink et al.
Neuroscience Lts. 188 (1995) 41–44, Davidson et al.

* cited by examiner

Primary Examiner—Floyd D. Higel
(74) Attorney, Agent, or Firm—Keil & Weinkauf

(57) ABSTRACT

A 3-substituted 3,4,5,6,7,8-hexahydropyrido[4',3':4,5]thieno [2,3-d]pyrimidine compound of formula I

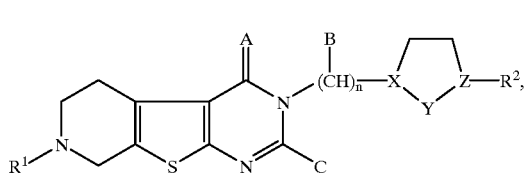

wherein $R^1$ is hydrogen, $C_1$–$C_4$-alkyl, acetyl or benzoyl, optionally substituted phenyl-$C_1$–$C_4$-alkyl, naphthyl-$C_1$–$C_3$-alkyl, phenyl-$C_2$–$C_3$-alkanone or a phenylcarbamoyl-$C_2$-alkyl, $R^2$ is optionally substituted phenyl, pyridyl, pyrimidyl or pyrazinyl, or an optionally substituted bicyclus wherein one of the two fused rings is a phenyl, a pyridyl, a pyrimidyl or a pyrazinyl ring, A is NH or oxygen, B is hydrogen or methyl, C is hydrogen, methyl or hydroxyl, X is nitrogen, Y is $CH_2$, $CH_2$—$C_2$, $CH_2$—$C_2$—$CH_2$ or $CH_2$—CH, Z is nitrogen, C or CH, and the linkage between Y and Z is a single or a double bond, and n is 2, 3 or 4, or a physiologically tolerated salt thereof, and compositions comprising them and their use as antagonists of $5HT_{1B}$ and $5HT_{1A}$ and for the treatment of depression and related disorders.

13 Claims, No Drawings

3-SUBSTITUTED PYRIDO[4',3':4,5]THIENO[2,3-D]PYRIMIDINE DERIVATIVES, THEIR PREPARATION AND THEIR USE

The invention relates to novel 3-substituted pyrido[4',3':4,5]thieno[2,3-d]pyrimidine derivatives, and the preparation and use thereof for producing pharmaceutical active substances.

Classical antidepressants and the newer selective serotonin reuptake inhibitors (SSRIs) display their antidepressant effect inter alia by inhibition of the active reuptake of the transmitter in the presynaptic nerve endings. Unfortunately, in these cases the antidepressant effect has its onset only after treatment for at least 3 weeks and, in addition, about 30% of patients are therapy-resistant.

Blockade of presynaptic serotonin autoreceptors increases, by abolition of the negative coupling, the serotonin release and thus the transmitter concentration present in the synaptic cleft. This increase in the transmitter concentration is regarded as the principle of the antidepressant effect. This mechanism of action differs from that of previously known antidepressants which activate both the presynaptic and somatodendritic autoreceptors and hence lead to a delayed onset of action only after desensitization of these autoreceptors. Direct autoreceptor blockade bypasses this effect.

According to current knowledge, the presynaptic serotonin autoreceptor is of the 5-$HT_{1B}$ subtype (Fink et al., Arch. Pharmacol. 352 (1995), 451). Selective blockade thereof by 5-$HT_{1B/D}$ antagonists increases the release of serotonin in the brain: G. W. Price et al., Behavioural Brain Research 73 (1996), 79–82; P. H. Hutson et al. Neuropharmacology 34 (1995), 383–392.

However, the selective 5-$HT_{1B}$ antagonist GR 127 935 surprisingly reduces release of serotonin in the cortex after systemic administration. One explanation might be stimulation of somatodendritic 5-$HT_{1A}$ receptors in the raphe region by the released serotonin, which inhibits the firing rate of serotonergic neurons and thus serotonin release (M. Skingle et al., Neuropharmacology 34 (1995), 377–382 and 393–402).

One strategy for bypassing the autoinhibitory effects in the serotonergic areas of origin thus pursues blockade of the presynaptic 5-$HT_{1B}$ receptors. This theory is supported by the observation that the effect of paroxetine on the release of serotonin in the dorsal raphe nucleus of the rat is potentiated by the 5-$HT_{1B}$ receptor antagonist GR 127 935 (Davidson and Stamford, Neuroscience Letts., 188 (1995),41).

The second strategy includes blockade of both types of autoreceptors, namely the 5-$HT_{1A}$ receptors, in order to enhance neuronal firing, and the 5-$HT_{1B}$ receptors, in order to raise terminal serotonin release (Starkey and Skingle, Neuropharmacology 33 (3–4) (1994), 393).

5-$HT_{1B/D}$ antagonists alone or coupled with a 5-$HT_{1A}$ receptor-antagonistic component ought therefore to augment the increase in serotonin release in the brain and might therefore have advantages in the treatment of depression and related psychological disorders.

It has now been found that 3-substituted 3,4,5,6,7,8-hexahydropyrido[4',3',:4,5]thieno[2,3-d]pyrimidine derivatives of the formula I

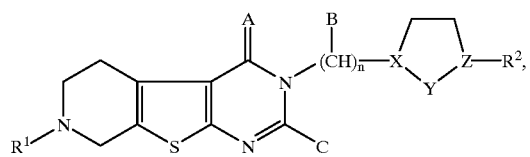

I where

R$^1$ is hydrogen, $C_1$–$C_4$-alkyl, acetyl or benzoyl, a phenylalkyl $C_1$–$C_4$ radical, the aromatic ring being unsubstituted or substituted by halogen, $C_1$–$C_4$-alkyl, trifluoromethyl, hydroxyl, $C_1$–$C_4$-alkoxy, amino, cyano or nitro groups, or is a naphthylalkyl $C_1$–$C_3$ radical, a phanylalkanone $C_2$–$C_3$ radical or a phenylcarbamoylalkyl $C_2$ radical, it being possible for the phenyl to be substituted by halogen, R$^2$ is phenyl, pyridyl, pyrimidinyl or pyrazinyl, each of which is unsubstituted or mono-, di- or trisubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups, and each of which may be fused to a benzene nucleus which may be unsubstituted or mono- or disubstituted by halogen atoms, $C_1$–$C_4$-alkyl, hydroxyl, trifluoromethyl, $C_1$–$C_4$-alkoxy, amino, cyano or nitro groups, and may contain 1 nitrogen atom, or to a 5- or 6-membered ring which may contain 1–2 oxygen atoms, or may be substituted by a phenyl-$C_1$–$C_2$-alkyl or -alkoxy group, it being possible for the phenyl to be substituted by halogen, a methyl, trifluoromethyl or methoxy group, A is NH or an oxygen atom, B is hydrogen or methyl, C is hydrogen, methyl or hydroxyl, X is a nitrogen atom, Y is CH$_2$, CH$_2$—C$_2$, CH$_2$—C$_2$—CH$_2$ or CH$_2$—CH, Z is a nitrogen atom, carbon atom or CH, it also being possible for the linkage between Y and Z to be a double bond, and n is 2, 3 or 4, and the salts thereof with physiologically tolerated acids, have valuable pharmacological properties.

Particularly preferred compounds are those where

R$^1$ is methyl, ethyl, isopropyl, benzyl, subst. benzyl, phenethyl, subst. phenethyl, R$^2$ is o-methoxyphenyl, 1-naphthyl, pyrimidin-2-yl, 2-methoxy-1-naphthyl, 2-methyl-1-naphthyl, A is NH or an oxygen atom, X is a nitrogen atom, Y is CH$_2$—C$_2$, CH$_2$—CH, Z is a nitrogen atom, carbon atom or CH, and n is 2 and 3.

Compounds of the formula I according to the invention can be prepared by reacting a compound of the formula II

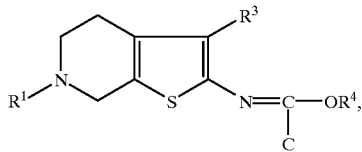

where $R^1$ has the abovementioned meaning, $R^3$ is cyano or a $C_{1-3}$-alkylcarboxylic ester group, $R^4$ is $C_{1-3}$-alkyl and C is hydrogen, methyl or hydroxyl, with a primary amine of the formula III

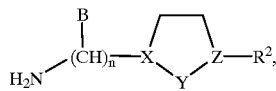

where $R^2$ and B have the abovementioned meanings, and converting the resulting compound where appropriate into the addition salt with a physiologically tolerated acid.

The reaction is expediently carried out in an inert organic solvent, in particular in a lower alcohol, eg. methanol or ethanol, or a cyclic saturated ether, in particular tetrahydrofuran or dioxane, or without solvent.

The reaction is, as a rule, carried out at from 20 to 190° C., in particular from 60 to 90° C., and is generally complete within 1 to 10 hours.

Or a compound of the formula II

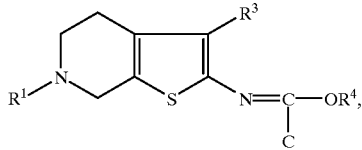

where $R^1$ has the abovementioned meaning, $R^3$ is cyano or a $C_{1-3}$-alkylcarboxylic ester group, $R^4$ is $C_{1-3}$-alkyl, and C is hydrogen, methyl or hydroxyl, is reacted with a primary amine of the formula IV

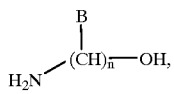

where B has the abovementioned meaning, in an inert solvent, preferably alcohols such as ethanol, at from 60 to 120° C. to give the cyclizdtion product V (D=OH)

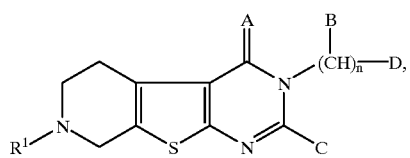

which is subsequently converted with a halogenating agent, eg. thionyl chloride or hydrobromic acid, in an organic solvent such as a halohydrocarbon or without solvent at from room temperature to 100° C. into the corresponding halo derivative V (D=Cl, Br). Finally, the halo derivative of the formula V (D=Cl, Br) is reacted with an amine of the formula VI

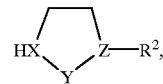

where X, Y, Z and $R^2$ have the abovementioned meanings, to give the final product of the formula I according to the invention. This reaction takes place best in an inert organic solvent, preferably toluene or xylene, in the presence of a base such as potassium carbonate or potassium hydroxide, at from 60 to 150° C.

The compounds of the formula I according to the invention can be either recrystallized by recrystallization from conventional organic solvents, preferably from a lower alcohol such as ethanol, or purified by column chromatography.

The free 3-substituted pyrido[4',3':4,5]thieno[2,3-d]pyrimidine derivatives of the formula I can be converted in a conventional way into acid addition salts by treatment with a solution containing the stoichiometric amount of the appropriate acid. Examples of pharmaceutically suitable acids are hydrochloric acid, phosphoric acid, sulfuric acid, methanesulfonic acid, sulfamic acid, maleic acid, fumaric acid, oxalic acid, tartaric acid or citric acid.

The invention accordingly also relates to a therapeutic composition which has a content of a compound of the formula I or pharmacologically suitable acid addition salt thereof as active substance in addition to conventional excipients and diluents, and to the use of the novel compounds for controlling diseases.

The compounds according to the invention can be administered in a conventional way orally or parenterally, intravenously or intramuscularly.

The dosage depends on the age, condition and weight of the patient and on the mode of administration. As a rule, the daily dose of active substance is about 1–100 mg/kg of body weight on oral administration and 0.1–10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. The active substances can for this purpose be processed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (Cf. H. Sucker et dl.; Pharmazeutische Technologie, Thieme-Verlag, Stuttgart, 1978). The administration forms obtained in this way normally contain from 1 to 99% by weight of active substance.

The substances of the formula II and III required as starting materials for synthesizing the novel compounds are known or can be synthesized by preparation methods described in the literature from appropriate starting materials (F. Sauter and P. Stanetty, Monatsh. Chem. 106 (5) (1975), 1111–1116; K. Gewald et al., Chem. Ber. 99 (1966), 94–100).

The compounds according to the invention have high affinity for $5\text{-HT}_{1B}$, $5\text{-HT}_{1D}$ and $5\text{-HT}_{1A}$ serotonin receptors.

The affinity is approximately the same, at least of the same order of magnitude, for each of these receptors. In addition, some of the compounds according to the invention show good inhibition of serotonin reuptake, a principle which is implemented in most antidepressants.

These compounds are suitable as drugs for the treatment of pathological states in which the serotonin concentration is reduced and in which it is wished for the purposes of treatment specifically to block the activity of the presynaptic $5\text{-HT}_{1B}$, $5\text{-HT}_{1A}$ and $5\text{-HT}_{1D}$ receptors without having a large effect on other receptors. An example of such a pathological state is depression.

The compounds of the present invention can also be of use for treating central nervous mood disturbances such as seasonal affective disorder an d dysthymia. These also include anxiety states such as generalized anxiety, panic attacks, sociophobia, obsessive-compulsive neuroses and post-traumatic stress symptoms, memory disturbances including dementia, amnesia and age-related loss of memory, and psychogenic eating disorders such as anorexia nervosa and bulimia nervosa.

The compounds according to the invention can additionally be of use for treating endocrine disorders such as hyperprolactinemia and for the treatment of vasospasms (especially of the cerebral vessels), hypertension and gastrointestinal disturbances associated with motility and secretory disturbances. Another area of use comprises sexual disorders.

The following examples serve to illustrate the invention:

A Preparation of the Starting Materials of the Formula II, V and VI

The 2-amino-3-carboethoxy(cyano)-4,5,6,7-tetrahydrothieno[2,3-c]pyridine with methyl, benzyl, acetyl or benzoyl in position 6 or with an unsubstituted position 6, which are employed as starting materials, are disclosed in the literature (K. Gewald et al.).

a) 2-Ethoxymethyleneamino-3-cyano-6-methyl-4, 5,6,7-tetrahydrothieno[2,3-c]pyridine 46.0 g (238 mmol) of 2-amino-3-cyano-6-methyl-4,5,6,7-tetrahydrothieno[2,3-c]pyridine in 250 ml of triethyl orthoformate were mixed with 3.5 ml of acetic anhydride and refluxed under nitrogen for 4 h. The mixture was then filtered hot under suction, and the filtrate was completely evaporated in a rotary evaporator at 80° C. The residue was taken up in 300 ml of methyl t-butyl ether and heated to boiling. After removal of the insoluble solids by filtration with suction, 45.4 g (77%) of product crystallized on stirring in an ice bath. 1.7 g (3%) of product were obtained as second fraction from the mother liquor. Melting point: 88–89° C.

b) 2-Ethoxymethyleneamino-3-carboethoxy-6-methyl-4, 5,6,7-tetrahydrothieno[2,3-c]pyridine 40.0 g (167 mmol) of 2-amino-3-carboethoxy-6-methyl-4,5,6,7-tetrahydrothieno[2,3-c]pyridine in 250 ml of triethyl orthoformate were mixed with 3.2 ml of acetic anhydride and refluxed under nitrogen for 3 h. The mixture was then completely evaporated in a rotary evaporator at 80° C. 48.0 g (97%) of crude product were isolated as a dark oil which is sufficiently pure for the next reaction.

c) 2-Amino-3-carboethoxy-6-(4-chloro)benzyl-4,5,6,7-tetrahydrothieno[2,3-c]pyridine 20.4 g (90.2 mmol) of 2-amino-3-carboethoxy-4,5,6,7-tetrahydrothieno[2,3-c]pyridine in 250 ml of tetrahydrofuran were mixed with 25.6 g (204 mmol) of 4-chlorobenzyl chloride and 12.4 g (90 mmol) of finely powdered potassium carbonate and refluxed for 3 h. The mixture was then completely evaporated in a rotary evaporator. The residue was partitioned between methyl t-butyl ether and water and, after making alkaline with sodium hydroxide solution, the organic phase was washed with water and concentrated. The crude product was dissolved in 100 ml of hot ethanol and left to crystallize with stirring. 20.5 g (65%) of product with melting point 134–135° C. were isolated.

d) 2-Ethoxymethyleneamino-3-carboethoxy-6-(4-chloro) benzyl-4,5,6,7-tetrahydrothieno[2,3-c]pyridine 19.3 g (55.0 mmol) of 2-amino-3-carboethoxy-6-(4-chlorobenzyl)-4,5,6,7-tetrahydrothieno[2,3-c] pyridine in 125 ml of triethyl orthoformate were mixed with 2.0 ml of acetic anhydride and refluxed under nitrogen for 1 h. The mixture was then completely evaporated in a rotary evaporator at 80° C. 21.9 g (98%) of crude product were isolated as a dark oil which is sufficiently pure for the next reaction.

e) 2-Amino-3-carboethoxy-6-(3-phenyl)propyl-4,5,6,7-tetrahydrothieno[2,3-c]pyridine 10.0 g (44.2 mmol) of 2-amino-3-carboethoxy-4,5,6,7-tetra-hydrothieno[2,3-c)pyridine [sic] in 100 ml of toluene were mixed with 9.0 g (45 mM) of 1-phenyl-3-bromopropane, 400 mg of potassium iodide and 6.1 g (44.2 mmol) of finely powdered potassium carbonate and refluxed for 6 h. The residue after concentration in a rotary evaporator was taken up in water, adjusted to pH=10 and extracted twice with methylene chloride. The crude product after drying and concentration of the organic phase was extracted by stirring in 50 ml of isopropanol. The pale solid was filtered off with suction and washed with isopropanol. 7.8 g (51%) of product with melting point 108–110° C. were isolated.

Other 4,5,6,7-tetrahydrothieno[2,3-c]pyridine derivatives substituted in position 6 were prepared as in c) and e), eg.:

2-amino-3-carboethoxy-6-ethyl-4,5,6,7-tetrahydrothieno[2, 3-c]pyridine, melting point 74–76° C.

2-amino-3-carboethoxy-6-isopropyl-4,5,6,7-tetrahydrothieno[2,3-c]pyridine 2-amino-3-carboethoxy-6-benzyl-4,5,6,7-tetrahydrothieno [2,3-c]pyridine, melting point 116–118° C.

2-amino-3-carboethoxy-6-(4-methyl)benzyl-4,5,6,7-tetrahydrothieno[2,3-c]pyridine 2-amino-3-carboethoxy-6-(4-nitro)benzyl-4,5,6,7-tetrahydrothieno[2,3-c]pyridine, melting point 170–172° C.

2-amino-3-carboethoxy-6-(4-methoxy)benzyl-4,5,6,7-tetrahydrothieno[2,3-c]pyridine, melting point 154–156° C.

2-amino-3-carboethoxy-6-(2-phenyl)ethyl-4,5,6,7-tetrahydrothieno[2,3-c]pyridine, melting point 80–83° C.

2-amino-3-carboethoxy-6-(2-(4-methoxyphenyl)ethyl)-4,5, 6,7-tetrahydrothieno[2,3-c]pyridine, melting point 76–78° C.

2-amino-3-carboethoxy-6-(2-(4-chlorophenyl)ethyl)-4,5,6, 7-tetrahydrothieno[2,3-c]pyridine, melting point 102–105° C.

2-amino-3-carboethoxy-6-(3-(4-chloro)phenyl)propyl-4,5, 6,7-tetrahydrothieno[2,3-c]pyridine 2-amino-3-carboethoxy-6-(4-phenyl)butyl-4,5,6,7-tetrahydrothieno[2,3-c]pyridine 2-amino-3-carboethoxy-6-(3-benzoyl)propyl-4,5,6,7-tetrahydrothieno[2,3-c]pyridine 2-amino-3-carboethoxy-6-(2-benzoylamino)ethyl-4,5,6,7-tetrahydrothieno[2,3-c]pyridine, melting point 190–192° C.

2-amino-3-carboethoxy-6-(3-benzoylamino)propyl-4,5,6,7-tetrahydrothieno[2,3-c]pyridine f) Ethyl N-(3-carboethoxy-6-methyl-4,5,6,7-tetrahydrothieno[2,3-c]pyridin-2-yl)ethanimidate 3.0 g (12.5 mmol) of 2-amino-3-carboethoxy-4,5,6,7-tetrahydrothieno[2,3-c]pyridine in 25 ml of triethyl orthoacetate were mixed with 0.8 ml of acetic anhydride and refluxed under nitrogen for 2 h. The mixture was then completely evaporated in a rotary evaporator at 80° C. 3.6 g (92%) of crude product were isolated as a dark oil which is sufficiently pure for the next reaction.

g) 2-Carboethoxyamino-3-carboethoxy-6-acetyl-4,5,6,7-tetrahydrothieno[2,3-c]pyridine 5.0 g (18.6 mmol) of 2-amino-3-carboethoxy-6-acetyl-4,5,6,7-tetrahydrothieno[2,3-c]pyridine in 50 ml of toluene were mixed with 3.0 g (28 mmol) of ethyl chloroformate and 2.6 g (18.6 mmol) of finely powdered potassium carbonate and refluxed for 2 h. The reaction mixture was then taken up in ice/water, the toluene phase was separated off, and the aqueous phase was back-extracted with toluene. The combined organic phases were dried and then concentrated. 5.8 g (92%) of product were isolated as an oil which slowly crystallizes somewhat.

h) 3,4,5,6,7,8-Hexahydro-3-(2-hydroxy)ethyl-7-methylpyrido[4',3':4,5]thieno[2,3-d]pyrimidin-4-one 86.4 g (292 mmol) of 2-ethoxymethyleneamino-3-carboethoxy-6-methyl-4,5,6,7-tetrahydrothieno[2,3-c]pyridine in 200 ml of ethanol were mixed with 17.6 ml (292 mmol) of ethanolamine and refluxed for 2 h. The mixture was then concentrated under reduced pressure, and the residue was taken up in 30 ml of ethyl acetate with stirring. The solid which precipitated overnight was filtered off with suction and washed with a little ethyl acetate. After recrystallization from ethanol, 48.0 g (62%) of product with melting point 163–165° C. were isolated.

i) 3,4,5,6,7,8-Hexahydro-3-(2-chloro)ethyl-7-methylpyrido[4',3':4,5]thieno[2,3-d]pyrimidin-4-one 42.0 g (158 mmol) of 3,4,5,6,7,8-hexahydro-3-(2-hydroxy)ethyl-7-methylpyrido[4',3':4,5]thieno[2,3-d]pyrimidin-4-one in 240 ml of 1,2-dichloroethane was heated to reflux and then 12.7 ml (175 mmol) of thionyl chloride in 20 ml of 1,2-dichloroethane were added dropwise. After refluxing for 2 h, the mixture was allowed to cool and was poured into ice/water. After partitioning between methylene chloride and water at pH=10, the aqueous phase was back-extracted with methylene chloride. The combined organic phases were dried and concentrated. The crude product (40 g) was recrystallized from 400 ml of isopropanol. 30.5 g (68%) of product with melting point 159–161° C. were isolated.

The following were prepared as in h) and i):

3,4,5,6,7,8-hexahydro-3-(1-hydroxy)prop-2-yl-7-methylpyrido[4',3':4,5]thieno[2,3-d]pyrimidin-4-one 3,4,5,6,7,8-hexahydro-3-(1-chloro)prop-2-yl-7-methylpyrido[4',3':4,5]thieno[2,3-d]pyrimidin-4-one 3,4,5,6,7,8-hexahydro-3-(2-hydroxy)propyl-7-methylpyrido[4',3':4,5]thieno[2,3-d]pyrimidin-4-one, m.p. 158–160° C.

3,4,5,6,7,8-hexahydro-3-(2-chloro)propyl-7-methylpyrido[4',3':4,5]thieno[2,3-d]pyrimidin-4-one k) N-(1-Naphthyl)piperazine 83.2 g (966 mmol) of piperazine, 38.0 g (339 mmol) of potassium tert-butoxide and 50.0 g (241 mmol) of 1-bromonaphthalene were added to a mixture of 5.4 g (24.2 mmol) of palladium acetate and 14.7 g (48.3 mmol) of tri-o-tolyl-phosphine in 500 ml of xylene, and the mixture was refluxed with efficient stirring under a nitrogen atomsphere for 10 h. The mixture was then diluted with methylene chloride, the insoluble residue was filtered off, and the filtrate was concentrated. The crude product was purified by column chromatography (silica gel, mobile phase THF/methanol/ammonia 85/13/2). 21.5 g (42%) of product with melting point 84–86° C. were isolated.

l) N-(2-Methyl-1-naphthyl)piperazine 13.0 g (82.7 mmol) of 1-amino-2-methylnaphthalene in 100 ml of chlorobenzene were mixed with 14.7 g (82.7 mmol) of bis(2-chloroethyl)amine×HCl and refluxed under nitrogen for 90 h. The mixture was then concentrated and partitioned between methylene chloride and water at pH=9, and the organic phase was dried and then concentrated. The crude product was purified by column chromatography (silica gel, mobile phase/THF/methanol/ammonia 85/13/2. 11.6 g (62%) of product were isolated.

m) 4-Piperazinyl-isoquinoline 4.51 g (21.7 mmol) of 4-bromoisoquinoline, 4.65 g (25.0 mmol) of t-butyl piperazine-N-carboxylate, 0.1 g (0.11 mmol) of tris(dibenzylideneacetone) dipalladium, 0.11 g (0.18 mmol) of 2,2'-bis (diphenylphosphino)-1,1'-binaphthyl and 2.92 g (30.4 mmol) of sodium t-butoxide were mixed in 50 ml of toluene and stirred at 75° C. for 2 h. The mixture was added to ice/sodium chloride and extracted with ethyl acetate, the organic phase was dried over sodium sulfate, and the solvent was removed in a rotary evaporator. The product crystallized out and was filtered off with suction and washed with pentane. 5.5 g (81%) of the Boc-protected piperazine (melting point 111° C.) were obtained. 5.2 g (16.6 mmol) of this substance were taken up in 17 ml of dichloromethane and, at 0° C. 17 ml (0.22 mmol) of trifluoroacetic acid were slowly added. The mixture was stirred at 0° C. for 4 h, poured into ice-water and extracted with dichloromethane. The aqueous phase wag filtered, made alkaline and extracted with dichloromethane. After drying over sodium sulfate, substantially removing the solvent and then diluting with diethyl ether, the hydrochloride was precipitated with etherial hydrochloric acid. 3.2 g (67%) of the product with melting point 293–294° C. were obtained.

Further piperazine derivatives (see examples) not disclosed in the literature (cf. also DE Patent Application 19636769.7) were prepared as in k), 1) and m).

B Preparation of the Final Products

EXAMPLE 1

3,4,5,6,7,8-Hexahydro-7-methyl-3-[2-(4-(2-methoxyphenyl)-1-piperazinyl)ethyl]pyrido[4',3':4,5]thieno[2,3-d]pyrimidin-4-imine×3 HCl 3.0 g (12.1 mmol) of 2-ethoxymethyleneamino-3-cyano-6-methyl-4,5,6,7-tetrahydrothieno[2,3-c]pyridine in 60 ml of ethanol were mixed with 3.3 g (12.1 mmol) of 1-(2-aminoethyl)-4-(2-methoxyphenyl)piperazine and refluxed for 3 h. The mixture was then evaporated in a rotary evaporator, and the residue was taken up in 100 ml of ethyl acetate. The trihydrochloride was precipitated by adding ethereal hydrochloric acid with stirring, and the product was filtered off with suction under nitrogen and washed with ethyl acetate. Drying at 50° C. in a vacuum oven resulted in isolation of 3.6 g (55%) of product which decomposed at 282–284° C.

EXAMPLE 2

3,4,5,6,7,8-Hexahydro-7-methyl-3-[2-(4-(2-methoxyphenyl)-1-piperazinyl)ethyl]pyrido[4',3':4,5]thieno[2,3-d]pyrimidin-4-one×3 HCl 3.0 g (12.1 mmol) of 2-ethoxymethyleneamino-3-carboethoxy-6-methyl-4,5,6,7-tetrahydrothieno[2,3-c]pyridine in 50 ml of ethanol were mixed with 2.4 g (10.2 mmol) of 1-(2-aminoethyl)-4-(2-methoxyphenyl)piperazine and refluxed for 3 h. The mixture was then evaporated in a rotary evaporator, and the crude product was purified by column chromatography (silica gel, mobile phase methylene chloride/methanol 93/7). The free base was converted as above into the trihydrochloride (3.2 g, 48%) which decomposed at 288–290° C.

EXAMPLE 3

3,4,5,6,7,8-Hexahydro-7-(4-chlorobenzyl)-3-[2-(4-(2-methoxyphenyl)-1-piperazinyl)ethyl]pyrido[4',3':4,5]thieno[2,3-d]pyrimidin-4-one×3 HCl 3.5 g (8.6 mmol) of 2-ethoxymethyleneamino-3-carboethoxy-6-(4-chlorobenzyl)-4,5,6,7-tetrahydrothieno[2,3-c]pyridine in 60 ml of ethanol were mixed with 2.0 g (8.6 mmol) of 1-(2-aminoethyl)-4-(2-methoxyphenyl)piperazine and refluxed for 4 h. The mixture was then evaporated in a rotary evaporator, and the crude product was purified by column chromatography (silica gel, mobile phase methylene chloride/methanol 95/5). The free base was converted as above into the trihydrochloride (3.2 g, 57%) which decomposed at 290–293° C.

EXAMPLE 4

3,4,5,6,7,8-Hexahydro-7-methyl-3-[3-(4-(2-methoxyphenyl)-1-piperazinyl)propyl]pyrido[4',3':4,5]thieno[2,3-d]pyrimidin-4-one×3 HCl×2 $H_2O$ 3.5 g (11.8 mmol) of 2-ethoxymethyleneamino-3-carboethoxy-6-methyl-4,5,6,7-tetrahydrothieno[2,3-c]pyridine in 40 ml of ethanol were mixed with 3.0 g (11.8 mmol) of 1-(3-aminopropyl)-4-(2-methoxyphenyl)piperazine and refluxed for 2 h. The mixture was then evaporated in a rotary evaporator, and the crude product was purified by column chromatography (silica gel, mobile phase methylene chloride/methanol 93/7). The free base was converted as above into the trihydrochloride (3.1 g, 44%) which decomposed at 122–124° C.

EXAMPLE 5

3,4,5,6,7,8-Hexahydro-7-methyl-3-[3-(4-pyridin-2-yl)-1-piperazinyl)propyl]pyrido[4',3':4,5]thieno[2,3-d]pyrimidin-4-imine×4 HCl×$H_2O$ 3.0 g (12.1 mmol) of 2-ethoxymethyleneamino-3-cyano-6-methyl-4,5,6,7-tetrahydrothieno[(2,3-c]pyridine in 60 ml of ethanol were mixed with 2.65 g (12.1 mmol) of 1-(3-aminopropyl)-4-(2-pyridinyl)piperazine and refluxed for 6 h. The mixture was then evaporated in a rotary evaporator, and the crude product was taken up in 100 ml of ethyl acetate. The solid which crystallized overnight was converted as above into the tetrahydrochloride. 2.7 g (38%) of product which decomposed at 261–264° C. were isolated.

EXAMPLE 6

3,4,5,6,7,8-Hexahydro-7-methyl-3-[3-(4-(2-thiomethylphenyl)-1-piperazinyl)propyl]pyrido[4',3':4,5]thieno[2,3-d]pyrimidin-4-imine×3 HCl 3.0 g (12.1 mmol) of 2-ethoxymethyleneamino-3-cyano-6-methyl-4,5,6,7-tetrahydrothieno[2,3-c]pyridine in 50 ml of ethanol were mixed with 3.2 g (12.1 mmol) of 1-(3-aminopropyl)-4-(2-thiomethylphenyl)piperazine and refluxed for 4 h. The mixture was then evaporated in a rotary evaporator, and the residue was taken up in 100 ml of boiling ethyl acetate. After cooling, the insolubles were filtered off, the trihydrochloride was precipitated from the filtrate by adding ethereal hydrochloric acid with stirring, and the product was filtered off with suction under nitrogen and washed with ethyl acetate. The crude product (5.1 g) was subsequently recrystallized from methanol. 3.8 g (54%) of product with melting point 306–307° C. were isolated.

EXAMPLE 7

3,4,5,6,7,8-Hexahydro-7-methyl-3-[2-(4-2-pyridinyl-1-piperazinyl)ethyl]pyrido[4',3':4,5]thieno[2,3-d]pyrimidin-4-one×3HCl×2$H_2O$ 2.2 g (7.8 mmol) of 3,4,5,6,7,8-hexahydro-3-(2-chloro)ethyl-7-methylpyrido[4',3':4,5]thieno[2,3-d]pyrimidin-4-one in 50 ml Of xylene were mixed with 1.6 g (10.0 mmol) of 1-(2-pyridyl)-piperazine, 1.4 g (10.0 mmol) of finely powdered potassium carbonate and 400 mg of potassium iodide and refluxed for 24 h. The mixture was then concentrated in a rotary evaporator, and the residue was partitioned between methylene chloride and water at pH=10. The aqueous phase was extraced once more with methylene chloride, and the combined organic hases were dried and then concentrated. The crude product was purified by column chromatography (silica gel, mobile phase acetone). 2.3 g (72%) of product were isolated and were dissolved in 100 ml of ethyl acetate and converted with HCl/ethyl acetate solution into the hydrochloride with melting point 233–235° C.

EXAMPLE 8

3,4,5,6,7,8-Hexahydro-7-methyl-3-[1-(4-(1-naphthyl)-1-piperazinyl)prop-2-yl]pyrido[4',3':4,5]thieno[2,3-d]pyrimidin-4-one×3HCl×2$H_2O$ 2.7 g (9.0 mmol) of 3,4,5,6,7,8-hexahydro-3-(1-chloro)-2-propyl-7-methylpyrido[4',3':4,5]thieno[2,3-d]pyrimidin-4-one in 50 ml of xylene were mixed with 2.1 g (10.0 mmol) of 1-(1-naphthyl)-piperazine, 1.4 g (10.0 mmol) of finely powdered potassium carbonate and 250 mg of potassium iodide and refluxed for 70 h. The mixture was then concentrated in a rotary evaporator, and the residue was partitioned between methylene chloride and water at pH=10. The aqueous phase was extracted once more with methylene chloride, and the combined organic phases were dried and then concentrated. The crude product was purified by column chromatography (silica gel, mobile phase acetone). 1.6 g (38%) of product were isolated and were dissolved in ethyl acetate and converted with HCl/ethyl acetate solution into the hydrochloride with melting point 242–244° C.

EXAMPLE 9

3,4,5,6,7,8-Hexahydro-7-methyl-3-[2-(4-(2-methoxyphenyl)-1-piperazinyl)propyl]pyrido[4',3':4,5]thieno[2,3-d]pyrimidin-4-one×3HCl 2.9 g (8.9 mmol) of 3,4,5,6,7,8-hexahydro-3-(2-chloro)propyl-7-methylpyrido[4',3':4,5]thieno[2,3-d]pyrimidin-4- one in 60 ml of xylene were mixed with 3.5 g (18.0 mmol) of 1-(2-methoxyphenyl)-piperazine, 1.4 g (10.0 mmol) of finely powdered potassium carbonate and 400 mg of potassium iodide and refluxed for 100 h. The mixture was then concentrated in a rotary evaporator, and the residue was partitioned between methylene chloride and water at pH=10. The aqueous phase was extracted once more with methylene chloride, and the combined organic phases were dried and then concentrated. The crude product was purified by column chromatography (silica gel, mobile phase acetone). 1.0 g (25%) of product was isolated and was dissolved in 100 ml of ethyl acetate and converted with HCl/ethyl acetate solution into the hydrochloride with melting point 190–192° C. (decomposition).

EXAMPLE 10

3,4,5,6,7,8-Hexahydro-2,7-dimethyl-3-[2-(4-(2-methoxyphenyl)-1-piperazinyl)-ethyl]-pyrido[4',3':4,5]thieno[2,3-d]pyrimidin-4-one 1.9 g (6.2 mmol) of ethyl N-(3-carboethoxy-6-methyl-4,5,6,7-tetrahydrothieno[2,3-c]pyridin-2-yl)ethanimidate in 30 ml of ethanol were mixed with 1.5 g (6.2 mmol) of 1-(2-aminoethyl)-4-(2-methoxyphenyl)piperazine and refluxed for 7 h. The mixture was then concentrated in a rotary evaporator, and the residue was taken up in 20 ml of ethyl acetate. 2.1 g of crude product crystallized out overnight and were filtered off with suction and purified by column chromatography (silica gel, mobile phase methylene chloride/methanol 92/8). 0.8 g (29%) of product was isolated.

EXAMPLE 11

3,4,5,6,7,8-Hexahydro-2-hydroxy-7-acetyl-3-[2-(4-(2-methoxyphenyl)-1-piperazinyl)ethyl]pyrido[4',3':4,5]thieno[2,3-d]pyrimidin-4-one 2.5 g (7.3 mmol) of 2-carboethoxyamino-3-carboethoxy-6-acetyl-4,5,6,7-tetrahydrothieno[2,3-c]pyridine were heated with 1.7 g (7.3 mmol) of 1-(2-aminoethyl)-4-(2-methoxyphenyl)piperazine at 180° C. for 2 h under nitrogen while stirring the melt efficiently. After cooling, the crude product was purified by column chromatography (silica gel, mobile phase methylene chloride/ methanol 95/5). 0.7 g (20%) of product with melting point 135–137° C. was isoldted.

EXAMPLE 12

3,4,5,6,7,8-Hexahydro-7-acetyl-3-[2-(4-(2-methoxyphenyl)-1-piperazinyl)ethyl]pyrido[4',3':4,5]thieno[2,3-d]pyrimidin-4-one 5.8 g (23.4 mmol) of 2-ethoxymethyleneamino-3-carboethoxy-6-acetyl-4,5,6,7-tetrahydrothieno[2,3-c]pyridine in 50 ml of ethanol were mixed with 5.5 g (23.4 mmol) of 1-(2-aminoethyl)-4-(2-methoxyphenyl)piperazine and refluxed for 2 h. The mixture was then concentrated in a rotary evaporator, and the residue was taken up in 30 ml of ethyl acetate, heated to boiling and left to cool with stirring. The solid which crystallized out was filtered off with suction after cooling in an ice bath and was washed with ethyl acetate. 8.7 g (80%) of product with melting point 170–172° C. were isolated.

EXAMPLE 13

3,4,5,6,7,8-Hexahydro-3-[2-(4-(2-methoxyphenyl)-1-piperazinyl)ethyl]pyrido[4',3'; 4,5]thieno[2,3-d]pyrimidin-4-one 4.0 g (8.6 mmol) of 3,4,5,6,7,8-hexahydro-7-acetyl-3-[2-(4-(2-methoxyphenyl)-1-piperazinyl)ethyl]pyrido[4',3':4,5]thieno[2,3-d]pyrimidin-4-one were dissolved in 80 ml of 10% strength hydrochloric acid and stirred at a bath temperature of 100° C. for 2 h. The mixture was then poured into ice-water, made alkaline with concentrated sodium hydroxide solution and extracted twice with methylene chloride. The combined organic phases were dried and concentrated. 3.7 g of crude product were isolated and were recrystallized from 50 ml of isopropanol. 2.4 g (66%) of product with melting point 168–170° C. were obtained.

EXAMPLE 14

3,4,5,6,7,8-Hexahydro-7-(2-(1-naphthyl)ethyl)-3-[2-(4-(2-methoxyphenyl)-1-piperazinyl)ethyl]pyrido[4',3':4,5]thieno[2,3-d]pyrimidin-4-one×3HCl 1.0 g (2.3 mmol) of 3,4,5,6,7,8-hexahydro-3-[2-(4-(2-methoxyphenyl)-1-piperazinyl)ethyl]pyrido[4',3':4,5]thieno[2,3-d]pyrimidin-4-one in 35 ml of xylene were mixed with 0.8 g (3.4 mmol) of 2-bromo-1-1-naphthyl-ethane and with 0.3 g (2.4 mmol) of finely powdered potassium carbonate and refluxed for 12 h. The mixture was then concentrated in a rotary evaporator, and the residue was partitioned between methylene chloride and water at pH=10. The aqueous phase was extracted once more with methylene chloride. The combined organic phases were dried and then concentrated. 2.7 g of crude product were obtained as a dark oil which was purified by column chromatography (silica gel, mobile phase methylene chloride/ acetone 7/3). After conversion into the hydrochloride in ethyl acetate, 1.0 g (63%) of product with melting point 293–295° C. (decomposition) was isolated.

The following were prepared in a similar manner to Examples 1 to 14:

15. 3,4,5,6,7,8-Hexahydro-7-methyl-3-[3-(4-(2-methoxyphenyl)-1-piperazinyl)propyl]pyrido[4',3':4,5]thieno[2,3-d]pyrimidin-4-imine, melting point 112–114° C.
16. 3,4,5,6,7,8-Hexahydro-7-benzyl-3-[3-(4-(2-methoxyphanyl)-1-piperazinyl)propyl]pyrido[4',3':4,5]thieno[2,3-d]pyrimidin-4-imine×2 HCl, melting point 258–261° C. (decomposition)
17. 3,4,5,6,7,8-Hexahydro-7-benzyl-3-[2-(4-phenyl-1-piperazinyl)ethyl]pyrido[4',3':4,5]thieno[2,3-d]pyrimidin-4-imine, melting point 162–170° C.
18. 3,4,5,6,7,8-Hexahydro-7-benzyl-3-[3-(4-(2-methoxyphenyl)-1-piperazinyl)propyl]pyrido[4',3':4,5]thieno[2,3-d]pyrimidin-4-one, melting point 66–67° C.
19. 3,4,5,6,7,8-Hexahydro-7-benzyl-3-[2-(4-phenyl-1-piperazinyl)ethyl]pyrido[4',3':4,5]thieno[2,3-d]pyrimidin-4-one, melting point 70–71° C.
20. 3,4,5,6,7,8-Hexahydro-7-methyl-3-[2-(4-2-pyrimidinyl-1-piperazinyl)ethyl]pyrido[4',3':4,5]thieno[2,3-d]pyrimidin-4-imine[sic]tritartrate, melting point 112–114° C. (decomposition)
21. 3,4,5,6,7,8-Hexahydro-7-methyl-3-[3-(4-(3-methoxyphenyl)-1-piperazinyl)propyl]pyrido[4',3':4,5]thieno[2,3-d]pyrimidin-4-imine×3 HCl×2 H$_2$O, melting point 268–270° C. (decomposition)
22. 3,4,5,6,7,8-Hexahydro-7-methyl-3-[3-(4-1-naphthyl-1-piperazinyl)propyl]pyrido[4',3':4,5]thieno[2,3-d]pyrimidin-4-imine×3 HCl, melting point 250–253° C. (decomposition)
23. 3,4,5,6,7,8-Hexahydro-7-methyl-3-[3-(4-(2-nitrophenyl)-1-piperazinyl)propyl]pyrido[4',3':4,5]thieno[2,3-d]pyrimidin-4-imine×3 HCl×2 H$_2$O, melting point 271–273° C. (decomposition)
24. 3,4,5,6,7,8-Hexahydro-7-methyl-3-[3-(4-(2-methyl)-1-piperazinyl)propyl]pyrido[4',3':4,5]thieno[2,3-d]

pyrimidin-4-imine×3 HCl, melting point 280–282° C. (decomposition)

25. 3,4,5,6,7,8-Hexahydro-7-methyl-3-[3-(4-(2-aminophenyl)-1-piperazinyl)propyl]pyrido[4',3':4,5]thieno[2,3-d]pyrimidin-4-imine×HCl×4 H₂O, melting point 113–115° C. (decomposition)

26. 3,4,5,6,7,8-Hexahydro-7-methyl-3-[3-(4-(2-chlorophenyl)-1-piperazinyl)propyl]pyrido[4',3':4,5]thieno[2,3-d]pyrimidin-4-imine×3 HCl, melting point 261–263° C. (decomposition)

27. 3,4,5,6,7,8-Hexahydro-7-methyl-3-[2-(4-2-pyrimidinyl-1-piperazinyl)ethyl]pyrido[4',3':4,5]thieno[2,3-d]pyrimidin-4-one, melting point 146–148° C.

28. 3,4,5,6,7,8-Hexahydro-7-methyl-3-[3-(4-benzyl-1-piperidinyl)propyl]pyrido[4',3':4,5]thieno[2,3-d]pyrimidin-4-imine×3HCl, melting point 295–297° C. (decomposition)

29. 3,4,5,6,7,8-Hexahydro-7-methyl-3-[3-(4-(2-hydroxyphenyl)-1-piperazinyl)propyl]pyrido[4',3':4,5]thieno[2,3-d]pyrimidin-4-imine, melting point 164–166° C.

30. 3,4,5,6,7,8-Hexahydro-7-methyl-3-[4-(4-(2-methoxyphenyl)-1-piperazinyl)butyl]pyrido[4',3':4,5]thieno[2,3-d]pyrimidin-4-imine×HCl×3 H₂O, melting point 272–274° C. (decomposition)

31. 3,4,5,6,7,8-Hexahydro-7-methyl-3-[3-(4-(2-ethoxyphenyl)-1-piperazinyl)propyl]pyrido[4',3':4,5]thieno[2,3-d]pyrimidin-4-imine×3 HCl×3 H₂O, melting point 284–286° C. (decomposition)

32. 3,4,5,6,7,8-Hexahydro-7-methyl-3-[3-(4-(2-ethylphenyl)-1-piperazinyl)propyl]pyrido[4',3':4,5]thieno[2,3-d]pyrimidin-4-imine×3 HCl, melting point 303–305° C. (decomposition)

33. 3,4,5,6,7,8-Hexahydro-7-methyl-3-[3-(4-(2-cyanophenyl)-1-piperazinyl)propyl]pyrido[4',3':4,5]thieno[2,3-d]pyrimidin-4-one×2 HCl×2 H₂O, melting point 136–138° C. (decomposition)

34. 3,4,5,6,7,8-Hexahydro-7-methyl-3-[3-(4-phenyl-1-piperindyl)propyl]pyrido[4',3':4,5]thieno[2,3-d]pyrimidin-4-imine×3 HCl, melting point 280–282° C. (decomposition)

35. 3,4,5,6,7,8-Hexahydro-7-methyl-3-[3-(4-2-pyrazinyl-1-piperazinyl)propyl]pyrido[4',3':4,5]thieno[2,3-d]pyrimidin-4-imine×4 HCl×H₂O, melting point 284–286° C. (decomposition)

36. 3,4,5,6,7,8-Hexahydro-7-methyl-3-[3-(4-2-pyrmidinyl-1-piperazinyl)propyl]pyrido[4', 3':4,5]thieno[2,3-d]pyrimidin-4-imine, melting point 161–163° C.

37. 3,4,5,6,7,8-Hexahydro-7-methyl-3-[3-(4-(2-cyanophenyl)-1-piperazinyl)propyl]pyrido[4',3':4,5]thieno[2,3-d]pyrimidin-4-imine, melting point 148–150° C. (decomposition)

38. 3,4,5,6,7,8-Hexahydro-7-benzyl-3-[2-(4-(2-methoxyphenyl)-1-piperazinyl)ethyl]pyrido[4',3':4,5]thieno[2,3-d]pyrimidin-4-one×3 HCl×H₂O, melting point 288–290° C. (decomposition)

39. 3,4,5,6,7,8-Hexahydro-7-methyl-3-[3-(4-(3,4-methylenedioxyphenyl)-1-piperazinyl)propyl]pyrido[4',3':4,5]thieno[2,3-d]pyrimidin-4-imine×3 HCl, melting point 288–290° C.

40. 3,4,5,6,7,8-Hexahydro-7-methyl-3-[2-(4-(2-methylphenyl)-1-piperazinyl)ethyl]pyrido[4',3':4,5]thieno[2,3-d]pyrimidin-4-one×2HCl×H₂O, melting point>300° C.

41. 3,4,5,6,7,8-Hexahydro-7-methyl-3-[2-(4-(2-chlorophenyl)-1-piperazinyl)ethyl]pyrido[4',3':4,5]thieno[2,3-d]pyrimidin-4-one×2HCl×H₂O, melting point>300° C.

42. 3,4,5,6,7,8-Hexahydro-7-methyl-3-[2-(4-(3,4-dimethylphenyl)-1-piperazinyl)ethyl]pyrido[4',3':4,5]thieno[2,3-d]pyrimidin-4-one×2HCl, melting point 307–310° C.

43. 3,4,5,6,7,8-Hexahydro-7-methyl-3-[2-(4-(2,6-dimethylphenyl)-1-piperazinyl)ethyl]pyrido[4',3':4,5]thieno[2,3-d]pyrimidin-4-one×2HCl, melting point 297–300° C.

44. 3,4,5,6,7,8-Hexahydro-7-methyl-3-[2-(4-(2,3-dimethylphenyl)-1-piperazinyl)ethyl]pyrido[4',3':4,5]thieno[2,3-d]pyrimidin-4-one, melting point 163–167° C.

45. 3,4,5,6,7,8-Hexahydro-7-methyl-3-[2-(4-(2,4-dimethylphenyl)-1-piperazinyl)ethyl]pyrido[4',3':4,5]thieno[2,3-d]pyrimidin-4-one×2HCl, melting point 300–303° C.

46. 3,4,5,6,7,8-Hexahydro-7-methyl-3-[2-(4-(3,5-dichlorophenyl)-1-piperazinyl)ethyl]pyrido[4',3':4,5]thieno[2,3-d]pyrimidin-4-one, melting point 97–100° C.

47. 3,4,5,6,7,8-Hexahydro-7-methyl-3-[2-(4-(2,4-dimethoxyphenyl)-1-piperazinyl)ethyl]pyrido[4',3':4,5]thieno[2,3-d]pyrimidin-4-one×2HCl, melting point 287–290° C.

48. 3,4,5,6,7,8-Hexahydro-7-methyl-3-[2-(4-(3-trifluoromethylphenyl)-1-piperazinyl)ethyl]pyrido[4',3':4,5]thieno[2,3-d]pyrimidin-4-one×2HCl, melting point 309–312° C.

49. 3,4,5,6,7,8-Hexahydro-7-methyl-3-[2-(4-naphth-1-yl-1-piperazinyl)ethyl]pyrido[4',3':4,5]thieno[2,3-d]pyrimidin-4-one×2HCl×H₂O, melting point 298–300° C. (decomposition)

50. 3,4,5,6,7,8-Hexahydro-7-methyl-3-[3-(4-(3-hydroxyphenyl)-1-piperazinyl)propyl]pyrido [4',3':4,5]thieno[2,3-d]pyrimidin-4-imine×2HCl×2H₂O, melting point 182–184° C. (decomposition)

51. 3,4,5,6,7,8-Hexahydro-7-methyl-3-[2-(4-(2-methoxy-5-chlorophenyl)-1-piperazinyl)ethyl]pyrido[4',3':4,5]thieno[2,3-d]pyrimidin-4-one×2HCl, melting point 170–172° C. (decomposition)

52. 3,4,5,6,7,8-Hexahydro-7-methyl-3-[2-(4-(2,5-dimethoxyphenyl)-1-piperazinyl)ethyl]pyrido[4',3':4,5]thieno[2,3-d]pyrimidin-4-one×3HCl×H₂O, melting point 176–178° C. (decomposition)

53. 3,4,5,6,7,8-Hexahydro-7-methyl-3-[2-(4-(2-methoxy-5-phenylphenyl)-1-piperazinyl)ethyl]pyrido[4',3':4,5]thieno[2,3-d]pyrimidin-4-one×H₂O, melting point 79–80° C.

54. 3,4,5,6,7,8-Hexahydro-7-methyl-3-[2-(4-(2-methoxyphenyl)-3,4-dehydropiperidin-1-yl)ethyl]pyrido[4',3':4,5]thieno[2,3-d]pyrimidin-4-one×2HCl×2H₂O, melting point 182–185° C. (decomposition)

55. 3,4,5,6,7,8-Hexahydro-7-methyl-3-[2-(4-(2-hydroxyphenyl)-1-piperazinyl)ethyl]pyrido[4',3':4,5]thieno[2,3-d]pyrimidin-4-one×2HCl×H₂O, melting point 281–283° C. (decomposition)

56. 3,4,5,6,7,8-Hexahydro-7-methyl-3-[2-(4-(7-methoxynaphth-1-yl)-1-piperazinyl)ethyl]pyrido[4',3':4,5]thieno[2,3-d]pyrimidin-4-one×2HCl×H₂O, melting point 272–274° C. (decomposition)

57. 3,4,5,6,7,8-Hexahydro-7-methyl-3-[2-(4-naphth-1-yl-1-piperazinyl)ethyl]pyrido[4',3':4,5]thieno[2,3-d]pyrimidin-4-imine×3HCl, melting point 288–289° C. (decomposition)

58. 3,4,5,6,7,8-Hexahydro-7-methyl-3-[2-(4-(4,5-methylenedioxy-benzyl)-1-piperazinyl)ethyl]pyrido[4',3':4,5]thieno[2,3-d]pyrimidin-4-imine×4HCl×2H₂O, melting point 249–251° C. (decomposition)

59. 3,4,5,6,7,8-Hexahydro-7-methyl-3-[2-(4-(6-isopropyl-pyrimidin-4-yl)-1-piperzinyl)ethyl]pyrido[4',3':4,5]

thieno[2,3-d]pyrimidin-4-imine×3HCl×2H$_2$O, melting point 250–253° C. (decomposition)

60. 3,4,5,6,7,8-Hexahydro-7-methyl-3-[2-(4-(2-methoxynaphth-1-yl)-1-piperazinyl)ethyl]pyrido[4',3':4,5]thieno[2,3-d]pyrimidin-4-one×2HCl×2H$_2$O, melting point 241–243° C. (decomposition)

61. 3,4,5,6,7,8-Hexahydro-7-methyl-3-[2-(4-(2-methoxyphenyl)-piperidin-1-yl)ethyl]pyrido[4',3':4,5]thieno[2,3-d]pyrimidin-4-one×2HCl×2H$_2$O, melting point 299–301° C. (decomposition)

62. 3,4,5,6,7,8-Hexahydro-7-methyl-3-[2-(4-(3,4-dimethoxyphenyl)-1-piperazinyl)ethyl]pyrido[4',3':4,5]thieno[2,3-d]pyrimidin-4-one, melting point 153–154° C.

63. 3,4,5,6,7,8-Hexahydro-7-methyl-3-[3-(4-naphth-1-yl-1-piperazinyl)propyl]pyrido[4',3':4,5]thieno[2,3-d]pyrimidin-4-one×3HCl×2H$_2$O, melting point 206–208° C. (decomposition)

64. 3,4,5,6,7,8-Hexahydro-7-methyl-3-[3-(4-pyrimidin-2-yl-1-piperazinyl)propyl]pyrido[4',3':4,5]thieno[2,3-d]pyrimidin-4-one, melting point 161–163° C.

65. 3,4,5,6,7,8-Hexahydro-7-methyl-3-[2-(4-quinolin-2-yl-1-piperazinyl)ethyl]pyrido[4',3':4,5]thieno[2,3-d]pyrimidin-4-one, melting point 143–145° C.

66. 3,4,5,6,7,8-Hexahydro-7-methyl-3-[2-(4-(2-methylnaphth-1-yl)ethyl]pyrido[4',3':4,5]thieno[2,3-d]pyrimidin-4-one ×2HCl×2H$_2$O, melting point 295–297° C. (decomposition)

67. 3,4,5,6,7,8-Hexahydro-7-methyl-3-[2-(4-(2-methoxy-3,5-dichlorophenyl)-1-piperazinyl)ethyl]pyrido[4',3':4,5]thieno[2,3-d]pyrimidin-4-one×2HCl×H$_2$O, melting point 264–267° C. (decomposition)

68. 3,4,5,6,7,8-Hexahydro-7-methyl-3-[2-(4-(2-cyanophenyl)piperazin-1-yl)ethyl]pyrido[4',3':4,5]thieno[2,3-d]pyrimidin-4-one, melting point 162–164° C.

69. 3,4,5,6,7,8-Hexahydro-7-methyl-3-[2-(4-(2-chlorophenyl)-1-piperazinyl)ethyl]pyrido[4',3':4,5]thieno[2,3-d]pyrimidin-4-one, melting point 165–167° C.

70. 3,4,5,6,7,8-Hexahydro-7-methyl-3-[2-(4-pyridin-2-yl-1-piperazinyl)ethyl]pyrido[4',3':4,5]thieno[2,3-d]pyrimidin-4-one×3HCl×2H$_2$O, melting point 232–234° C. (decomposition)

71. 3,4,5,6,7,8-Hexahydro-7-methyl-3-[2-(4-pyridin-4-yl-1-piperazinyl)ethyl]pyrido[4',3':4,5]thieno[2,3-d]pyrimidin-4-one×3HCl×2H$_2$O, melting point 270–272° C. (decomposition)

72. 3,4,5,6,7,8-Hexahydro-7-methyl-3-[2-(4-(5-methoxypyrimidin-4-yl)-1-piperazinyl)ethyl]pyrido[4',3':4,5]thieno[2,3-d]pyrimidin-4-one×3HCl×4H$_2$O, melting point 266–268° C. (decomposition)

73. 3,4,5,6,7,8-Hexahydro-7-methyl-3-[2-(4-naphth-2-yl-1-piperazinyl)ethyl]pyrido[4',3':4,5]thieno[2,3-d]pyrimidin-4-one, melting point 140–141° C.

74. 3,4,5,6,7,8-Hexahydro-7-methyl-3-[2-(4-pyrazin-2-yl-1-piperazinyl)ethyl]pyrido[4',3':4,5]thieno[2,3-d]pyrimidin-4-one×3HCl×3H$_2$O, melting point 170–172° C. (decomposition)

75. 3,4,5,6,7,8-Hexahydro-7-methyl-3-[2-(4-tetralin-5-yl-1-piperazinyl)ethyl]pyrido[4',3':4,5]thieno[2,3-d]pyrimidin-4-one×3HCl×2H$_2$O, melting point 285–287° C. (decomposition)

76. 3,4,5,6,7,8-Hexahydro-7-methyl-3-[2-(4-indan-1-yl-1-piperazinyl)ethyl]pyrido[4',3':4,5]thieno[2,3-d]pyrimidin-4-one ×3HCl×2H$_2$O, melting point 300–301° C. (decomposition)

77. 3,4,5,6,7,8-Hexahydro-7-methyl-3-[2-(4-(2-methoxy-4-nitro-5-methylphenyl)-1-piperazinyl)ethyl]pyrido[4',3':4,5]thieno[2,3-d]pyrimidin-4-one×2HCl×2H$_2$O, melting point 210–212° C. (decomposition)

78. 3,4,5,6,7,8-Hexahydro-7-methyl-3-[2(4-4-isoquinolinyl-1-piperazinyl)ethyl]pyrido[4',3':4,5]thieno[2,3-d)]pyrimidin-4-one×3HCl×3H$_2$O, melting point 290–292° C. (decomposition)

79. 3,4,5,6,7,8-Hexahydro-7-methyl-3-[2-(4-(2-methoxy-4-chloro-5-methylphenyl)-1-piperazinyl)ethyl]pyrido[4',3':4,5]thieno[2,3-d]pyrimidin-4-one×2HCl×2H$_2$O, melting point 293–294° C. (decomposition)

80. 3,4,5,6,7,8-Hexahydro-7-methyl-3-[2-(4-(2,4-dimethoxyphenyl)-1-piperazinyl)ethyl]pyrido[4',3':4,5]thieno[2,3-d ]pyrimidin-4-one×3HCl×3H$_2$O, melting point 290–291° C. (decomposition)

81. 3,4,5,6,7,8-Hexahydro-7-methyl-3-[2-(4-4-quinazolinyl-1-piperazinyl)ethyl]pyrido[4',3':4,5]thieno[2,3-d]pyrimidin-4-one×3HCl×4H$_2$O, melting point 258–260° C. (decomposition)

82. 3,4,5,6,7,8-Hexahydro-7-methyl-3-[2-(4-(3-trifluoromethyl-4-chlorophenyl)-1-piparazinyl)ethyl]pyrido[4',3':4,5]thieno[2,3-d]pyrimidin-4-one×2HCl×3H$_2$O, melting point 311–312° C. (decomposition)

83. 3,4,5,6,7,8-Hexahydro-7-(4-chlorobenzyl)-3-[2-(4-(2-methoxyphenyl)-1-piperazinyl)ethyl]pyrido[4',3':4,5]thieno[2,3-d]pyrimidin-4-one×3HCl×H$_2$O, melting point 290–292° C. (decomposition)

84. 3,4,5,6,7,8-Hexahydro-7-ethyl-3-[2-(4-(2-methoxyphenyl)-1-piperazinyl)ethyl]pyrido[4',3':4,5]thieno[2,3-d]pyrimidin-4-one×3HCl×H$_2$O, melting point 295–297° C. (decomposition)

85. 3,4,5,6,7,8-Hexahydro-7-isopropyl-3-[2-(4-(2-methoxyphenyl)-1-piperazinyl)ethyl]pyrido[4',3':4,5]thieno[2,3-d]pyrimidin-4-one×3HCl×H$_2$O, melting point 300–302° C. (decomposition)

86. 3,4,5,6,7,8-Hexahydro-7-(4-nitro)benzyl-3-[2-(4-(2-methoxyphenyl)-1-piperazinyl)ethyl]pyrido[4',3':4,5]thieno[2,3-d]pyrimidin-4-one×3HCl×H$_2$O, melting point 214–217° C. (decomposition)

87. 3,4,5,6,7,8-Hexahydro-7-(4-methoxy)benzyl-3-[2-(4-(2-methoxyphenyl)-1-piperazinyl)ethyl]pyrido[4',3':4,5]thieno[2,3-d]pyrimidin-4-one×3HCl×H$_2$O, melting point 278–281° C. (decomposition)

88. 3,4,5,6,7,8-Hexahydro-7-(2-phenyl)ethyl-3-[2-(4-(2-methoxyphenyl)-1-piperazinyl)ethyl]pyrido[4',3':4,5]thieno[2,3-d]pyrimidin-4-one×3HCl×H$_2$O, melting point 305–306° C. (decomposition)

89. 3,4,5,6,7,8-Hexahydro-7-(3-benzoyl)propyl-3-[2-(4-(2-methoxyphenyl)-1-piperazinyl)ethyl]pyrido[4',3':4,5]thieno[2,3-d]pyrimidin-4-one×3HCl×H$_2$O, melting point 124–126° C. (decomposition)

90. 3,4,5,6,7,8-Hexahydro-7-(4-amino)benzyl-3-[2-(4-(2-methoxyphenyl)-1-piperazinyl)ethy]pyrido[4',3':4,5]thieno[2,3-d]pyrimidin-4-one×HCl×3H$_2$O, melting point 280–282° C. (decomposition)

91. 3,4,5,6,7,8-Hexahydro-7-(3-phenyl)propyl-3-[2-(4-(2-methoxyphenyl)-1-piperazinyl)ethyl]pyrido[4',3':4,5]thieno[2,3-d]pyrimidin-4-one×2HCl×3H$_2$O, melting point 301–302° C. (decomposition)

92. 3,4,5,6,7,8-Hexahydro-7-(3-phenyl)propyl-3-[2-(4-naphth-1-yl)-1-piperazinyl)ethyl]pyrido[4',3':4,5]thieno[2,3-d]pyrimidin-4-one[sic]×2HCl×2H$_2$O, melting point 306–307° C. (decomposition)

93. 3,4,5,6,7,8-Hexahydro-7(2-(4-mothoxy)phenyl)ethyl-3-[2-(4 -naphth-1-yl)-1-piperazinyl)ethyl]pyrido[4',3':4,5]thieno[2,3-d]pyrimidin-4-one×2HCl×3H$_2$O, melting point 306–308° C. (decomposition)

94. 3,4,5,6,7,8-Hexahydro-7-(2-(4-chloro)phenyl)ethyl-3-[2-(4-naphth-1-yl)-1-piperazinyl)ethyl]pyrido[2,3-d]pyrimidin-4-one 2HCl×3H$_2$O, melting point 300–303° C. (decomposition)

95. 3,4,5,6,7,8-Hexahydro-7-(2-phenyl)ethyl-3-[2-(4-naphth-1-yl)-1-piperazinyl)ethyl]pyrido[4',3':4,5]thieno[2,3-d ]pyrimidin-4-one×2HCl×3H$_2$O, melting point 295–298° C.
96. 3,4,5,6,7,8-Hexahydro-7-(2-(4-hydroxy)phenyl)ethyl-3-[2-(4-naphth-1-yl)-1-piperazinyl)ethyl]pyrido[4',3':4,5]thieno[2,3-d]pyrimidin-4-one×2HCl×2H$_2$O, melting point 254–256° C.
97. 3,4,5,6,7,8-Hexahydro-7-(2-(4-chloro)phenyl)ethyl-3-[2-(4-(2-methoxyphenyl)-1-piperazinyl)ethyl]pyrido[4',3':4,5]thieno[2,3-d]pyrimidin-4-one×3HCl×2H$_2$O, melting point 304–306° C. (decomposition)
98. 3,4,5,6,7,8-Hexahydro-7-(2-naphth-1-yl)ethyl-3-[2-(4-(2-methoxyphenyl)-1-piperazinyl )ethyl]pyrido[4',3':4,5]thieno[2,3-d]pyrimidin-4-one×2HCl×2H$_2$O, melting point 293–295° C. (decomposition)
99. 3,4,5,6,7,8-Hexahydro-7-(2-benzoylamino)ethyl-3-[2-(4-naphth-1-yl)-1-piperazinyl)ethyl]pyrido[4',3':4,5]thieno[2,3-d]pyrimidin-4-one×2HCl×2H$_2$O, melting point 292–294° C. (decomposition)
100. 3,4,5,6,7,8-Hexahydro-7-(2-benzoylamino)ethyl-3-[2-(4-(2-methoxyphenyl)-1-piperazinyl)ethyl]pyrido[4',3':4,5]thieno[2,3-d]pyrimidin-4-one×2HCl×3H$_2$O, melting point 202–204C. (decomposition)
101. 3,4,5,6,7,8-Hexahydro-7-(3-benzoylamino)propyl-3-[2-(4-(2-methoxyphenyl)-1-piperazinyl)ethyl]pyrido[4',3':4,5]thieno[2,3-d]pyrimidin-4-one×3HCl×2H$_2$O, melting point 182–183° C. (decomposition)
102. 3,4,5,6,7,8-Hexahydro-7-(3-benzoylamino)propyl-3-[2-(4-(naphth-1-yl)-1-piperazinyl)ethyl]pyrido[4',3':4,5]thieno[2,3-d]pyrimidin-4-one×3HCl×H$_2$O, melting point 129–130° C. (decomposition)
103. 3,4,5,6,7,8-Hexahydro-7-(4-phenyl)butyl-3-[2-(4-(2-methoxyphenyl)-1-piperazinyl)ethyl]pyrido[4',3':4,5]thieno[2,3-d]pyrimidin-4-one×3HCl×H$_2$O, melting point 311–312° C. (decomposition)
104. 3,4,5,6,7,8-Hexahydro-7-(4-phenyl)butyl-3-[2-(4-naphth-1-yl)-1-piperazinyl)ethyl]pyrido[4',3':4,5]thieno[2,3-d]pyrimidin-4-one×3HCl×H$_2$O, melting point 312–314° C. (decomposion)
105. 3,4,5,6,7,8-Hexahydro-7-(4-methoxy)benzyl-3-[2-(4-naphth-1-yl)-1-piperazinyl)ethyl]pyrido[4',3':4,5]thieno[2,3-d]pyrimidin-4-one×3HCl×H$_2$O, melting point 275–277° C. (decomposition)
105. 3,4,5,6,7,8-Hexahydro-7-(2-(4-methoxy)phenyl)ethyl-3-[2-(4-(2-methoxyphenyl)-1-piperazinyl)ethy]pyrido[4',3':4,5]thieno[2,3-d]pyrimidin-4-one×3HCl×3H$_2$O, melting point 297–298° C. (decomposition)
107. 3,4,5,6,7,8-Hexahydro-7-(2-phenyl)ethyl-3[(3-(4-naphth-1-yl)-1-piperazinyl)propyl]pyrido[4',3':4,5]thieno[2,3-d]pyrimidin-4-one, melting point 153–155° C.
108. 3,4,5,6,7,8-Hexahydro-7-(2-phenyl)ethyl-3-[2-(4-pyrimidin-2-yl)-1-piperazinyl)ethyl)pyrido[4',3':4,5]thieno[2,3-d]pyrimidin-4-one×2HCl×3H$_2$O, melting point 304–305° C. (decomposition)
109. 3,4,5,6,7,8-Hexahydro-7-(2-phenyl)ethyl-3-[3-(4-pyrimidin-2-yl)-1-piperazinyl)propyl)pyrido[4',3':4,5]thieno[2,3-d]pyrimidin-4-one×3HCl×2H$_2$O, melting point 302–303° C. (decomposition)
110. 3,4,5,6,7,8-Hexahydro-7-(3-benzoylamino)propyl-3-[2-(4-pyrimidin-2-yl)-1-piperazinyl)ethyl)pyrido[4',3':4,5]thieno[2,3-d]pyrimidin-4-one×3HCl×3H$_2$O, melting point 125–127° C. (decomposition)
111. 3,4,5,6,7,8-Hexahydro-7-(4-phenyl)butyl-3-[2-(4-pyrimidin-2-yl)-1-piperazinyl)ethyl)pyrido[4',3':4,5]thieno[2,3-d]pyrimidin-4-one×3HCl×3H$_2$O, melting point 317–319° C. (decomposition)
112. 3,4,5,6,7,8-Hexahydro-7-(2-(4-methoxy)phenyl)ethyl-3-[2-(4-pyrimidin-2-yl)-1-piperazinyl)ethylpyrido[4',3':4,5]thieno[2,3-d]pyrimidin-4-one, melting point 165–167° C.
113. 3,4,5,6,7,8-Hexahydro-7-acetyl-3-[3-(4-(2-methoxyphenyl)-1-piperazinyl)propyl]pyrido[4',3':4,5]thieno[2,3-d]pyrimidin-4-imine×2HCl, melting point 265–268° C.
114. 3,4,5,6,7,8-Hexahydro-7-acetyl-3-[3-(4-(2-methoxyphenyl)-1-piperazinyl)propyl]pyrido[4',3':4,5]thieno[2,3-d]pyrimidin-4-one×2HCl×2H$_2$O, melting point 264–267° C.
115. 3,4,5,6,7,8-Hexahydro-3-[2-(4-(2-methoxyphenyl)-1-piperzinyl)ethyl]pyrido[4',3';4,5]thieno[2.3-d]pyrimidin-4-one, melting point 168–170° C.
116. 3,4,5,6,7,8-Hexahydro-7-acetyl-3-[2-(4-(2-methoxyphenyl)-1-piperazinyl)ethyl]pyrido[4',3':4,5]thieno[2,3-d]pyrimidin-4-one, melting point 170–172° C.
117. 3,4,5,6,7,8-Hexahydro-7-benzoyl-3-[2-(4-(2-methoxyphenyl)-1-piperazinyl)ethyl]pyrido[4',3':4,5]thieno[2,3-d]pyrimidin-4-one×2HCl×2H$_2$O, melting point 185–187° C. (decomposition)
118. 3,4,5,6,7,8-Hexahydro-7-benzoyl-3-[2-(4-naphth-1-yl)-1-piperazinyl)ethyl]pyrido[4',3':4,5]thieno[2,3-d]pyrimidin-4-one, melting point 195–197° C.
119. 3,4,5,6,7,8-Hexahydro-7-benzoyl-3-[2-(4-pyrimidin-2-yl)-1-piperazinyl)ethyl]pyrido[4',3':4,5]thieno[2,3-d]pyrimidin-4-one, melting point 130–132° C. (decomposition)
120. 3,4,5,6,7,8-Hexahydro-2,7-dimethyl-3-[2-(4-(2-methoxyphenyl)-1-piperazinyl)ethyl]pyrido[4',3':4,5]thieno[2,3-d]pyrimidin-4-one, melting point 176–178° C.
121. 3,4,5,6,7,8-Hexahydro-7-acetyl-2-hydroxy-3-[2-(4-(2-methoxyphenyl)-1-piperazinyl)ethyl]pyrido[4',3':4,5]thieno[2,3-d]pyrimidin-4-one, melting point 135–137° C.
122. 3,4,5,6,7,8-Hexahydro-7-methyl-3-[1-(4-(2-methoxyphenyl)-1-piperazinyl)prop-2-yl]pyrido[4',3':4,5]thieno[2,3-d]pyrimidin-4-one, melting point 184–186° C.
123. 3,4,5,6,7,8-Hexahydro-(1-(4-naphth-1-yl-1-piperazinyl)-prop-2-yl]pyrido[4',3':4,5]thieno[2,3-d]pyrimidin-4-one [sic]×2HCl×4H$_2$O, melting point 242–244° C. (decomposition)
124. 3,4,5,6,7,8-Hexahydro-7-methyl-3-[2-(4-(2-methoxyphenyl)-1-piperazinyl)propyl]pyrido[4',3':4,5]thieno[2,3-d]pyrimidin-4-one×3HCl×3H$_2$O, melting point 190–192° C. (decomposition)

C Measurement of Receptor Binding

Preparation of the Receptor-bearing Cell Membranes

The receptor binding studies were carried out with membrane preparations obtained from cell cultures of the human embryonic kidney cell line 293 (HEK 293) into each of which a specific serotonin receptor subtype (h5HT1A, h5HT1B or h5HT1D) is cloned and is permanently expressed.

The cells were grown in RPMI 1640 medium (Life Technologies) which additionally contained 10% fetal calf serum (FCS), 2 mmol/l L-glutamine and 400 mg/l Geneticin G 418. The cells were incubated in a tray stack under air/5% $CO_2$ in an incubator at 37° C. until a continuous monolayer of cells was obtained. The cells were then detached from the culture vessels using a buffer of the following composition: (amounts per liter) trypsin 10 mg; EDTA 4 mg; EGTA 200 mg; KCl 200 mg; $KH_2PO_4$ 200 mg; $Na_2HPO_4$ 1.15 g; NaCl 8.0 g; pH 7.4. The cell suspension was pelleted and resuspended in Dulbecco's phosphate-buffered saline (PBS) and the cell density was adjusted to about $10^8$ cells/ml. After renewed pelleting, PBS was replaced by the same volume of ice-cold lysis buffer (5 mmol/l tris; 10% glycerol; pH 7.4) and incubated at 4° C. for 30 min. The lyzed cells (=membranes) were stored in aliquots in liquid nitrogen until used in receptor binding studies. One aliquot of each preparation was used to determine the protein content.

The compounds according to the invention show a high affinity ($K_i \leq 30$ nM) for human $5\text{-HT}_{1A}$, $5\text{-HT}_{1B}$ and $5\text{-HT}_{1D}$ receptor types expressed in cloned cell lines.

Receptor Binding Assay

The receptor binding studies were carried out in 1 ml macrowell tubes which contained the following components:

50 μl of the test substance in various concentrations for competition measurements or 50 μl of assay buffer or 50 μl of unlabeled serotonin (1 μmol/l final) to determine the total or nonspecific binding control 200 μl of membrane suspension of the appropriate receptor subtype with a protein content of 200 μg/tube 250 μl of radioligand solution ([³H]5-carboxamidotryptamine (5-CT) for h5HT1B and h5HT1D receptors or [³H]8-hydroxydiproplyminotetralin 8-OH-DPAT) for h5HT1A receptors. The final concentrations of the radioligands were adjusted to 3 nmol/l and 0.3 nmol/l respectively.

The assay buffer (pH 7.4) has the following composition (per liter): tris 6.057 g; $CaCl_2 \times 2H_2O$=5.88 g; ascorbic acid 1 g; pargyline 1.96 mg.

The assay mixture was incubated at 25° C. for 30 min and then filtered through fiberglass filters (Whatman GF/B) using a cell harvesting apparatus (Skatron) and the filters were washed with 5 to 9 ml of cold buffer. The filters were mixed in scintillation vials with, in each case, 5 ml of Ultima GoldxR liquid scintillator (Packard) and shaken for 1 hour, and then the radioactivity was determined in a beta counter (Wallac). The measured data were subjected to iterative nonlinear regression analysis using the statistical analysis system (SAS), which is similar to the LIGAND program described by Munson and Rodbard (Anal. Biochem: 107, 220 (1980) ). The competition constants ($K_i$) have been indicated in nmol/l.

We claim:

1. A 3-substituted 3,4,5,6,7,8-hexahydropyrido[4',3':4,5]thieno[2,3-d]pyrimidine compound of formula I

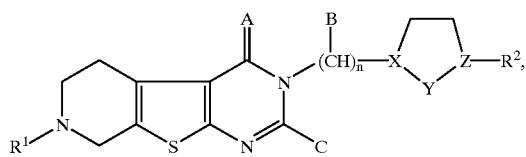

wherein

R¹ is hydrogen, $C_1$–$C_4$-alkyl, acetyl or benzoyl, a phenylalkyl $C_1$–$C_4$ radical, wherein the aromatic ring is unsubstituted or substituted by halogen, $C_1$–$C_4$-alkyl, trifluoromethyl, hydroxyl, $C_1$–$C_4$-alkoxy, amino, cyano or nitro groups, a naphthylalkyl $C_1$–$C_3$ radical, a phenylalkanone $C_2$–$C_3$-radical or a phenylcarbamoylalkyl $C_2$ radical, wherein the phenyl ring is unsubstituted or substituted by halogen, R² is phenyl, pyridyl, pyrimidyl or pyrazinyl, each of which is unsubstituted or carries substituents selected from the group consisting of:
(i) one to three of the following: halogen, $C_1$–$C_4$-alkyl, trifluoromethyl, trifluoromethoxy, hydroxyl, $C_1$–$C_4$-alkoxy, amino, monomethylamino, dimethylamino, cyano and nitro, and
(ii) one phenyl-$C_1$–$C_2$-alkyl or phenyl-$C_1$–$C_2$-alkoxy, wherein the phenyl ring is unsubstituted or substituted by halogen, methyl, trilfuoromethyl or methoxy, or
is one of the foregoing unsubstituted or substituted phenyl, pyridyl, pyrimidyl or pyrazinyl radicals wherein two adjacent ring carbon atoms are bridged to form a benzo-fused or a pyridino-fused bicyclus wherein the bridging moiety is unsubstituted or substituted by one or two substituents selected from the group consisting of: halogen, $C_1$–$C_4$-alkyl, hydroxyl, trifluoromethyl, $C_1$–$C_4$-alkoxy, amino, cyano and nitro, or
is one of the foregoing unsubstituted or substituted phenyl, pyridyl, pyrimidyl or pyrazinyl radicals wherein two adjacent ring carbon atoms are bridged to form a 5- or 6-membered ring consisting of carbon ring members or carbon ring members and one or two oxygen atoms as ring members, A is NH or an oxygen atom, B is hydrogen or methyl, C is hydrogen, methyl or hydroxyl, X is a nitrogen atom, Y is $CH_2$, $CH_2$—$C_2$, $CH_2$—$C_2$—$CH_2$ or $CH_2$—CH, Z is a nitrogen atom, carbon atom or CH, wherein the linkage between Y and Z is a single or a double bond, and n is 2, 3 or 4, or a physiologically tolerated salt thereof.

2. The compound defined in claim 1, wherein

R¹ is methyl, ethyl, isopropyl, benzyl, substituted benzyl, phenethyl or substituted phenethyl, R² is o-methoxyphenyl, 1-naphthyl, pyrimidin-2-yl, 2-methoxy-1-naphthyl or 2-methyl-1-naphthyl, X is a nitrogen atom, Y is $CH_2$—$C_2$ or $CH_2$—CH, and n is 2 or 3.

3. A composition for the treatment of depression or central nervous mood disturbances in which the serotonin concentration in the synaptic cleft is reduced comprising an effective amount of the compound of formula I defined in claim 1 or its salt and at least one pharmaceutical auxiliary.

4. A pharmaceutical composition comprising an effective amount of the compound of formula I defined in claim 1 or its salt as a selective $5HT_{1B}$ and $5HT_{1A}$ serotonin receptor antagonist, and at least one pharmaceutical auxiliary.

5. The composition defined in claim 3, wherein

R¹ is methyl, ethyl, isopropyl, benzyl, substituted benzyl, phenethyl or substituted phenethyl, R² is o-methoxyphenyl, 1-naphthyl, pyrimidin-2-yl, 2-methoxy-1-naphthyl or 2-methyl-1-naphthyl, X is a nitrogen atom, Y is $CH_2$—$CH_2$ or $CH_2$—CH, and n is 2 or 3.

6. The composition defined in claim 4, wherein

R¹ is methyl, ethyl, isopropyl, benzyl, substituted benzyl, phenethyl or substituted phenethyl, R² is o-methoxyphenyl, 1-naphthyl, pyrimidin-2-yl, 2-methoxy-1-naphthyl or 2-methyl-1-naphthyl, X is a nitrogen atom, Y is $CH_2$—$CH_2$ or $CH_2$—CH, and n is 2 or 3.

7. The composition defined in claim 4, wherein

R¹ is methyl, ethyl, isopropyl, benzyl, substituted benzyl, phenethyl or substituted phenethyl, R² is o-methoxyphenyl, 1-naphthyl, pyrimidin-2-yl, 2-methoxy-1-naphthyl or 2-methyl-1-naphthyl, X is a nitrogen atom, Y is $CH_2$—$CH_2$ or $CH_2$—CH, and n is 2 or 3.

8. A method for the treatment of depression or central nervous mood disturbances in which the serotonin concentration in the synaptic cleft is reduced in a patient, which comprises administering an effective amount of the compound of formula I defined in claim 1 or its salt to the patient.

9. The method defined in claim 8, wherein

R¹ is methyl, ethyl, isopropyl, benzyl, substituted benzyl, phenethyl or substituted phenethyl, R² is o-methoxyphenyl, 1-naphthyl, pyrimidin-2-yl, 2-methoxy-1-naphthyl or 2-methyl-1-naphthyl, X is a nitrogen atom, Y is $CH_2$—$CH_2$ or $CH_2$—CH, and n is 2 or 3.

10. A method for the selective antagonization of $5HT_{1B}$ and $5HT_{1A}$ serotonin receptor in a patient, which comprises administering an effective amount of the compound of formula I defined in claim 1 or its salt to the patient.

11. The method defined in claim 10, wherein

R¹ is methyl, ethyl, isopropyl, benzyl, substituted benzyl, phenethyl or substituted phenethyl, R² is o-methoxyphenyl, 1-naphthyl, pyrimidin-2-yl, 2-methoxy-1-naphthyl or 2-methyl-1-naphthyl, X is a nitrogen atom, Y is $CH_2$—$CH_2$ or $CH_2$—CH, and n is 2 or 3.

12. The method defined in claim 10, further comprising an inhibition of the serotonin re-uptake into the presynaptic nerve endings, which comprises administering an effective amount of the compound of formula I or its salt to the patient.

13. The method defined in claim 12, wherein

R¹ is methyl, ethyl, isopropyl, benzyl, substituted benzyl, phenethyl or substituted phenethyl, R² is o-methoxyphenyl, 1-naphthyl, pyrimidin-2-yl, 2-methoxy-1-naphthyl or 2-methyl-1-naphthyl, X is a nitrogen atom, Y is $CH_2$—$CH_2$ or $CH_2$—CH, and n is 2 or 3.

* * * * *

UNITED STATES PATENT AND TRADEMARK OFFICE
CERTIFICATE OF CORRECTION

PATENT NO. : 6,222,034 B1
DATED : April 24, 2001
INVENTOR(S) : Steiner et al.

Page 1 of 1

It is certified that error appears in the above-identified patent and that said Letters Patent is hereby corrected as shown below:

ABSTRACT,
Line 8, from the bottom, "$CH_2,C_2$-$CH_2,C_2$-CH," should be -- $CH_2$-$CH_2$-$CH_2$-$CH_2$-$CH_2$ --.

Column 20, claim 1,
Line 10, "trilfuoromethyl" should be -- trifluoromethyl --.
Line 32, "$CH_2,C_2$-$CH_2,C_2$-CH," should be -- $CH_2$-$CH_2$-$CH_2$-$CH_2$-$CH_2$ --.

Column 20, claim 2,
Line 45, "$CH_2$-$C_2$" should be -- $CH_2$-$CH_2$ --.

Signed and Sealed this

Eighteenth Day of December, 2001

Attest:

Attesting Officer

JAMES E. ROGAN
Director of the United States Patent and Trademark Office